(12) United States Patent
Reuschel et al.

(10) Patent No.: US 11,561,211 B2
(45) Date of Patent: Jan. 24, 2023

(54) TEST CHAMBER AND A METHOD FOR ITS CONTROL

(71) Applicant: WEISS UMWELTTECHNIK GMBH, Reiskirchen (DE)

(72) Inventors: Dennis Reuschel, Gießen (DE); Bjoern Stroh, Gemuenden (DE)

(73) Assignee: WEISS TECHNIK GMBH, Reiskirchen (DE)

( * ) Notice: Subject to any disclaimer, the term of this patent is extended or adjusted under 35 U.S.C. 154(b) by 182 days.

(21) Appl. No.: 17/162,697

(22) Filed: Jan. 29, 2021

(65) Prior Publication Data
US 2021/0239668 A1 Aug. 5, 2021

(30) Foreign Application Priority Data

Jan. 31, 2020 (EP) ..................................... 20154912

(51) Int. Cl.
*G01N 33/00* (2006.01)
*F25B 9/00* (2006.01)
*G01N 1/42* (2006.01)

(52) U.S. Cl.
CPC ......... *G01N 33/0016* (2013.01); *F25B 9/008* (2013.01); *G01N 1/42* (2013.01); *F25B 2309/061* (2013.01)

(58) Field of Classification Search
CPC ...... G01N 33/0016; G01N 1/42; F25B 9/008; F25B 2309/061; F25B 1/10; F25D 31/005
See application file for complete search history.

(56) References Cited

U.S. PATENT DOCUMENTS

| 2,434,221 A | 1/1948 | Newton |
| 5,062,274 A | 11/1991 | Shaw |

(Continued)

FOREIGN PATENT DOCUMENTS

| EP | 0344397 A2 | 12/1989 |
| JP | S5442058 A | 4/1979 |

*Primary Examiner* — Francis C Gray
(74) *Attorney, Agent, or Firm* — Quarles & Brady LLP (57) ABSTRACT

A test chamber and a method for conditioning air in a temperature-insulated test space of a test chamber, which is sealable against an environment and serves for receiving test material, a temperature ranging from −20° C. to +180° C. being produced within the test space by means of a cooling device of a temperature control device of the test chamber, using a cooling circuit with carbon dioxide ($CO_2$) as a cooling agent, using a heat exchanger in the test space, using a low-pressure compressor and using a high-pressure compressor downstream of the low-pressure compressor, using a gas cooler, using a storage means for the cooling agent and using an expansion valve, the temperature in the test space being controlled and/or regulated by means of a control device of the test chamber. A gaseous and/or liquid cooling agent is dosed in the storage means by means of a high-pressure valve of the cooling circuit downstream of the gas cooler, the storage means being connected to a medium-pressure side of the cooling circuit upstream of the high-pressure compressor and downstream of the low-pressure compressor via a medium-pressure bypass of the cooling circuit, the gaseous cooling agent being dosed in the medium-pressure side from the storage means by means of a medium-pressure valve when the low-pressure compressor is switched off.

20 Claims, 3 Drawing Sheets

(56) References Cited

U.S. PATENT DOCUMENTS

| | | | | |
|---|---|---|---|---|
| 5,351,499 | A * | 10/1994 | Takemasa | C09K 5/045 252/67 |
| 6,161,391 | A * | 12/2000 | Trieskey | F25B 40/02 62/79 |
| 7,320,228 | B2 * | 1/2008 | Kamimura | F25B 41/37 62/510 |
| 2008/0127672 | A1 * | 6/2008 | Ducoulombier | F25B 40/00 62/504 |
| 2009/0301109 | A1 * | 12/2009 | Manole | F25B 9/008 62/175 |
| 2010/0115975 | A1 * | 5/2010 | Mitra | F25B 1/10 700/282 |
| 2011/0023514 | A1 * | 2/2011 | Mitra | F25B 1/10 62/513 |
| 2011/0138825 | A1 * | 6/2011 | Chen | F25B 49/02 62/115 |
| 2017/0010051 | A1 * | 1/2017 | Connolly | F25B 9/008 |
| 2018/0328628 | A1 | 11/2018 | Sun et al. | |
| 2019/0093926 | A1 * | 3/2019 | Haack | F25B 9/006 |

* cited by examiner

TEST CHAMBER AND A METHOD FOR ITS CONTROL

This application claims priority to European Patent Application no. 20154912.8 filed Jan. 31, 2020, the contents of which are hereby incorporated by reference in their entirety.

The disclosure relates to a test chamber, in particular a climate chamber for conditioning air, and to a method for conditioning air in a temperature-insulated test space of a test chamber, which is sealable against an environment and serves for receiving test material, a temperature ranging from −20° C. to +180° C. being produced within the test space by means of a cooling device of a temperature control device of the test chamber, using a cooling circuit with carbon dioxide as a cooling agent, using a heat exchanger in the test space, using a low-pressure compressor and using a high-pressure compressor downstream of the low-pressure compressor, using a gas cooler, using a storage means for the cooling agent and using an expansion valve, the temperature in the test space being controlled and/or regulated by means of a control device of the test chamber.

Test chambers of this kind are commonly employed for checking physical and/or chemical properties of objects, in particular devices. Hence, temperature test chambers or climate test chambers are known within which temperatures ranging from −70° C. to +180° C. can be set. In climate test chambers, desired climate conditions can be additionally set to which the device or the test material is exposed over a defined period of time. A temperature of the test space receiving the test material to be tested is commonly controlled in an air-circulation duct within the test space. The air-circulation duct forms an air-treatment space in the test space in which heat exchangers are disposed for heating or cooling the air flowing through the air-circulation duct and the test space. A fan or a ventilator suctions the air in the test space and guides it in the air-circulation duct to the corresponding heat exchangers. The temperature of the test material can be controlled or the test material be exposed to a defined change in temperature. During a test interval, a temperature can fluctuate between a temperature maximum and a temperature minimum of the test chamber, for example. Such a test chamber is disclosed in EP 0 344 397 A2, for example.

The cooling agent used in a cooling circuit should have a fairly low $CO_2$ equivalent, i.e., a relative greenhouse potential or global warming potential (GWP) should be as low as possible in order to prevent unintended damage to the environment via the release of the cooling agent. Consequently, the use of carbon dioxide ($CO_2$) as a pure-element cooling agent has been known. Carbon dioxide is cheaply available, is incombustible and is essentially environmentally neutral at a GWP of 1. Carbon dioxide has a freezing temperature or triple-point of −56.6° C., wherefore lower temperatures cannot be attained using only carbon dioxide.

Moreover, cooling devices are known which are realized as what is known as a booster installation. In a cooling circuit of the cooling devices, a high-pressure compressor is always switched in series downstream of a low-pressure compressor, meaning that the cooling agent is gradually compressed using the low-pressure compressor and subsequently the high-pressure compressor. Due to the high demands regarding a temperature regulation within the temperature range of the test space, a load requirement regularly fluctuates during operation of the test chamber. A cooling capacity produced by the compressors and the expansion valve must therefore be continuously variable. Nevertheless, it is desirable that the compressors should not be switched on and off frequently to prolong their service life.

To compensate small differences in temperature between an actual temperature and a target temperature, it has been known to guide a mass flux in the cooling circuit caused by the compressors past the heat exchanger via a bypass to avoid unfavorable load instances at the compressors and thus a frequent switching-on and off of the compressors. The disadvantage here, however, is that the compressors always need to be in operation when the difference in temperature at the heat exchanger is small, independently of how large the difference in temperature to be compensated by the cooling device is. If a cooling capacity of a total capacity is >1%, for example, the full cooling capacity of the corresponding compressor must be made available in order to be able to maintain the required target temperature at the heat exchanger. A majority of the cooling capacity is then guided back to the compressor via the bypass described above. As a continued switching-on and off of the compressor is not possible, and if need be a fan has to be operated at the condenser or gas cooler, a comparatively large energy consumption of the cooling device and a shortened service life of the compressors are the result even for very low differences in temperature to be compensated when the known mode of operation described above is employed.

The object of the disclosure at hand is therefore to propose a method for conditioning air in a test space of a test chamber as well as a test chamber, which both enable a more economic operation of the test chamber.

This object is attained by a method having the features of claim 1 and a test chamber having the features of claim 17.

In the method according to the disclosure for conditioning air in a temperature-insulated test space of a test chamber, which is sealable against an environment and serves for receiving test material, a temperature ranging from −20° C. to +180° C. is produced within the test space by means of a cooling agent of a temperature control device of the test chamber, using a cooling circuit with carbon dioxide as a cooling agent, using a heat exchanger in the test space, using a low-pressure compressor and using a high-pressure compressor downstream of the low-pressure compressor, using a gas cooler, using a storage means for the cooling agent and using an expansion valve, the temperature in the test space being controlled and/or regulated by means of a control device of the test chamber. A gaseous and/or liquid cooling agent is dosed in the storage means by means of a high-pressure valve of the cooling circuit downstream of the gas cooler, the storage means being connected to a medium-pressure side of the cooling circuit upstream of the high-pressure compressor and downstream of the low-pressure compressor via a medium-pressure bypass of the cooling circuit, the gaseous cooling agent being dosed in the medium-pressure side from the storage means by means of a medium-pressure side when the low-pressure compressor is switched off.

The method according to the disclosure allows largely preventing a heat exchange with an environment of the test space by temperature-insulating side walls, bottom walls and top walls. The heat exchanger is connected to or integrated in the cooling circuit in such a manner that a cooling agent circulating in the cooling circuit flows through the heat exchanger. The heat exchanger of the cooling circuit is disposed within the test space or in an air-treatment space of the test space, meaning that air is conditioned and controlled in temperature in the test space via the heat exchanger. The gas cooler is also integrated in the cooling circuit and realized as a heat exchanger. The gas cooler is disposed in the cooling circuit downstream of the high-pressure compressor, the compressed cooling agent, which is highly pressurized after being compressed and is essentially gaseous, being able to condense in the gas cooler or condenser and is available in an essentially liquid state. It is also possible that the gaseous cooling agent does not condense in the gas cooler and leaves the gas cooler in an essentially gaseous state. The gas cooler and the corresponding heat exchanger can be equipped with means for cooling the cooling agent, for example using air or water. The gaseous and/or liquid cooling agent flows from the gas cooler to the storage means via the high-pressure valve. Depending on the sampling point in the storage means, an either liquid or gaseous cooling agent can be sampled from the storage means. The liquid cooling agent is further guided via the expansion valve, the liquid cooling agent becoming liquid again by expanding in consequence of a drop in pressure. In doing so, the cooling agent flows through the heat exchanger whereby it is cooled. Subsequently, the gaseous cooling agent is suctioned by the low-pressure compressor and/or high-pressure compressor and compressed.

The disclosure at hand intends for the high-pressure valve to be downstream of the gas cooler in the cooling circuit and for a gaseous and/or liquid cooling agent to be dosed in the storage means via the high-pressure valve. The storage means is essentially a pressure container in which the liquid cooling agent is stored in a lower area and the gaseous cooling agent in an upper area of the pressure container when forming a phase boundary. From the storage means, a liquid or gaseous cooling agent is sampled depending on where the sampling point is located on the storage means. Thus, a liquid cooling agent can be guided to the expansion valve and can expand there to cool the heat exchanger. An expansion valve is understood to at least be an expansion means, a throttle or a throttle valve or a different kind of suitable constriction of a fluid line. The expansion valve or the medium-pressure valve and the high-pressure valve as well as other valves of the cooling circuit are preferably realized so as to be regulatable.

If only a low cooling capacity is required, e.g., less than 2% of the cooling capacity of the cooling circuit, and/or if temperatures in the test space are lower than ≥−10° C., switching off the low-pressure compressor is intended. A cooling capacity of the cooling cycle is understood to be a thermal energy or a heat energy or even a heat content in joule, an addition of heat increasing a thermal energy and a removal of heat decreasing a thermal energy. A heat removal at the heat exchanger via the cooling circuit consequently corresponds to a corresponding cooling capacity of the cooling circuit. Since a capacity of the compressor is hardly regulatable, the low-pressure compressor is switched off and the high-pressure compressor continues in operation when a low cooling capacity is required and/or the difference between a target temperature and an actual temperature in the test space is small in order to be able to quickly provide a possibly required higher cooling capacity. The continued operation of the high-pressure compressor is enabled by the storage means being connected to the medium-pressure side of the cooling circuit upstream of the high-pressure compressor and downstream of the low-pressure compressor via the medium-pressure bypass. The medium-pressure bypass is connected in such a manner to the storage means at a sampling point that the gaseous cooling agent can be sampled from the storage means. A dose of the gaseous cooling agent can be dispensed from the storage means in the medium-pressure side as required by means of the medium-pressure valve disposed in the medium-pressure bypass. The high-pressure compressor can now continue in operation if no or a very low cooling capacity is required and/or if only a slight difference in temperature needs to be compensated in the test space. Thus, on the one hand, an operational availability can be ensured by the continued operation of the high-pressure compressor and, on the other hand, the low-pressure compressor can be switched off over longer periods of time and frequent power-on intervals are avoided. Since the entire running time of the compressor and switch cycles are decreased thus, the test chamber can be operated to be particularly energy efficient and have a long service life.

A temperature ranging from −40° C. to +180° C., preferably −55° C. to +180° C., can be produced within the test space by means of the temperature control device. If particularly low temperatures of >−10° C. are to be produced in the test space, it can be intended to operate the high-pressure compressor in conjunction with the low-pressure compressor. In this case, the medium-pressure valve can be closed for a short period of time and the cooling agent can be liquified and guided to the storage means via the gas cooler. Generally, however, it is intended to keep the medium-pressure valve open so that a certain amount of gaseous cooling agent can be guided in the medium-pressure side at any given time. An entrance temperature of the cooling agent at the gas cooler can lie below the critical point of the cooling agent so that the cooling agent is liquified in the gas cooler. In the event that there is too little gaseous cooling agent in the storage means for regulating the capacity of the cooling device via the medium-pressure bypass, a pressure can be reduced below a condensation temperature of the cooling agent via the high-pressure valve at short notice so that the cooling agent is no longer liquified in the gas cooler. This operating state can be maintained until a sufficient amount of gaseous cooling agent is available again in the storage means.

The low-pressure compressor can be switched off by the control device if a target temperature ranges from −10° C. to +180° C., preferably 0° C. to +180° C. Provided that a particularly large cooling capacity is required in this temperature range, an operation of the low-pressure compressor is not required and energy can be saved. In this instance the cooling agent can be guided via a bypass past the low-pressure compressor to the high-pressure compressor, for example.

Advantageously, the cooling circuit can be operated in a thermodynamically subcritical, transcritical or supercritical operating state. Depending on the required cooling capacity or the difference in temperature between an actual temperature and a target temperature to be attained in the test space, the cooling circuit can be operated in one of these operating states. The operating state of the cooling circuit generally depends on an entrance temperature of the cooling agent of the gas cooler at the gas cooler, the cooling agent being cooling water or air, for example. In the subcritical operation of the cooling circuit, the cooling agent is liquified in the gas cooler below the critical point of the cooling agent, is expanded at the expansion valve and transitions to the gaseous state. At least in the subcritical operating state, the high-pressure compressor and the low-pressure compressor can be operated. In the transcritical and the supercritical operating state, the cooling agent circulates in the cooling circuit in an essentially gaseous state. This means that a difference in temperature is reduced so far that the cooling agent is not liquified in the gas cooler. A pressure above the critical point of the cooling agent is also produced at the gas cooler in the transcritical state.

In the supercritical operating state, the cooling agent can expand at the high-pressure valve and can be guided in the storage means as a gaseous cooling agent. The gas cooler itself can be cooled using air or water, for example, so that the cooling agent is also cooled when flowing through the gas cooler. The gas cooler can then be realized as a heat exchanger. It can also be ensured that the cooling agent exits the gas cooler at least partially, preferably entirely, gaseous. In the transcritical operating state, however, a portion of the cooling agent can be liquid, in which case it is then intended that this portion is comparatively large. The cooling agent can be entirely gaseous on the high-pressure side in the transcritical operating state; a portion of the cooling agent turns liquid only when it expands via the high-pressure valve. The gaseous and possibly liquid cooling agent is guided in the storage device via the high-pressure valve, the portion of the liquid cooling agent in the storage means being gradually increased in the transcritical state.

In the transcritical operating state, the high-pressure valve can be regulated in such a manner by means of the control device that partially gaseous and liquid cooling agent is guided in the storage means. Consequently, a regulation of the high-pressure valve is intended to decrease a pressure at the gas cooler so far or to increase a gas exit temperature at the gas cooler so far that the cooling agent is no longer or only partially liquified in the gas cooler. The cooling agent is still gaseous when exiting the gas cooler; when it expands, it can be more or less liquid depending on the pressure and the temperature at the entrance of the high-pressure valve.

When the cooling agent expands via the high-pressure valve, the cooling agent can be gaseous, the transcritical operating state being able to be maintained for as lang as gaseous cooling agent is available in the storage means and can be guided to the medium-pressure side upstream of the high-pressure compressor via the medium-pressure bypass.

Consequently, a capacity of the high-pressure compressor can be adjusted as a function of a target temperature, the medium-pressure valve being able to be regulated in such a manner by means of the control device in the supercritical state that the gaseous agent is guided in the medium-pressure side. The gaseous cooling agent can be suctioned and compressed by the high-pressure compressor so that the high-pressure compressor can continue in operation even though no or only little cooling capacity is required. Generally, a portion of the gaseous cooling agent can be guided in the medium-pressure side in all operating states. In addition, the capacity of the high-pressure compressor can also be adjusted by adjusting a conveyor capacity of the high-pressure compressor, for example via a frequency converter if the high-pressure compressor is a compressor.

A second medium-pressure bypass having at least one second medium-pressure valve can be realized in the cooling circuit, the second medium-pressure bypass being able to be connected to the cooling circuit downstream of the storage device and upstream of the expansion valve and downstream of the low-pressure valve and upstream of the high-pressure compressor, the liquid cooling agent being able to be dosed in the medium-pressure side from the storage device by means of the second medium-pressure valve. This enables the cooling agent to cool in the medium-pressure area. If the cooling agent is heated via the low-pressure compressor upon compression, the cooled cooling agent can then be supplied to the high-pressure compressor. The second medium-pressure valve can be realized as an injection valve, for example, via which the liquid cooling agent can be injected in the medium-pressure area. The second medium-pressure bypass can be connected to the storage means in such a manner that only liquid cooling agent is sampled from the storage means.

Furthermore, a low-pressure bypass having at least one second expansion valve can be realized in the cooling circuit, the low-pressure bypass being connected to the cooling circuit downstream of the storage means and upstream of the expansion valve and downstream of the heat exchanger and upstream of the low-pressure compressor, the liquid cooling agent being dosed in a low-pressure side from the storage means by means of the second expansion valve. A low-pressure side of the cooling circuit can be realized downstream of the expansion valve and upstream of the low-pressure compressor. Since the heat exchanger is in the test space, the cooling agent can flow from the heat exchanger to the low-pressure compressor and the high-pressure compressor at a temperature of, for example, +180° C. when temperatures are particularly high in the test space. Before the highly heated cooling agent is supplied to the compressors, the cooling agent can be cooled by the cooling agent dosed via the second expansion valve.

A regulating bypass having at least one regulating valve can be formed in the cooling circuit, the regulating bypass being able to be connected to the cooling circuit downstream of the heat exchanger and upstream of the low-pressure compressor and downstream of the low-pressure compressor and upstream of the high-pressure compressor, the gaseous cooling agent being able to be dosed in a low-pressure side by means of the regulating valve, the low-pressure compressor being able to be in operation. For instance, the low-pressure compressor can be operated at a temperature range of $\leq -10°$ C. in conjunction with the high-pressure compressor, the regulating valve initially being able to be entirely closed. The regulating valve can then be used for regulating a capacity of the low-pressure compressor by the cold gaseous cooling agent being guided from the medium-pressure side back to the low-pressure side. In this case, injecting liquid cooling agent into the low-pressure side, for example via a low-pressure bypass, can be omitted.

The control device can set a suction pressure in such a manner by means of the regulating bypass that the cooling agent is in a state below the triple-point upstream of the low-pressure compressor. By omitting to inject liquid cooling agent into the low-pressure side and to supply cold gaseous cooling agent from the medium-pressure side, a suction pressure upstream of the low-pressure compressor can be lowered to the triple-point without any dry ice forming. This is particularly advantageous for long suction lines for compensating pressure losses via the suction line and for ensuring that the difference between the temperature in the test space and a temperature of the heat exchanger or an evaporation temperature of the cooling agent is sufficient enough when temperatures in the test space are low.

In the cooling circuit, a regulating bypass having at least one regulating valve can be realized, the regulating bypass being able to be connected to the cooling circuit downstream of the heat exchanger and upstream of the low-pressure compressor and downstream of the low-pressure compressor and upstream of the high-pressure compressor, the gaseous cooling agent being able to be dosed in the medium-pressure side from a low-pressure side by means of the regulating valve, the low-pressure compressor then being able to be switched off. Consequently, providing a cooling capacity via the high-pressure compressor and switching off the low-pressure compressor is sufficient when a temperature is in the range of $\geq -10°$ C. in the test space. The regulating valve can then be entirely opened so that the low-pressure side and the medium-pressure side are connected to each other. A mass flow of the cooling agent can be guided past the low-pressure compressor to the high-pressure compressor. The regulating valve can also be employed for regulating a pressure on the low-pressure side. Accordingly, the regulating bypass having the regulating valve can be used for different operating states of the cooling device, namely in a temperature range from −10° C. to −55° C. by sampling the cold gaseous cooling agent from the medium-pressure side and injecting it in the low-pressure side upstream of the low-pressure compressor, a low suction pressure below the triple-point being possible, or for regulating the pressure on the low-pressure side or in the heat exchanger if the low-pressure compressor is switched off in a climate operation and/or for regulating the capacity of the low-pressure compressor if the low-pressure compressor and the high-pressure compressor are used simultaneously. A suction pressure of the high-pressure compressor is regulated via the medium-pressure valve.

The temperature control device can also comprise a dehumidifier which is made up of a dehumidifier bypass having a dehumidifying valve and an additional heat exchanger in the test space, the dehumidifier bypass being connected to the storage device and to the medium-pressure side downstream of the low-pressure compressor and upstream of the high-pressure compressor, the cooling agent being dosed in the medium-pressure side from the storage device by means of the dehumidifier valve if the low-pressure compressor is switched off or on. The additional heat exchanger can form what is known as a wet dehumidifier which is also disposed in the test space, the heat exchanger commonly being intended to have a lower temperature with respect to the heat exchanger so that condensation occurs at the additional heat exchanger and not at the heat exchanger. The dehumidifier valve can be an expansion valve via which the liquid cooling agent expands in the additional heat exchanger. The cooling agent exiting from the additional heat exchanger can be substantially gaseous and enters the medium-pressure side downstream of the low-pressure compressor. Since the dehumidifier bypass is connected to the medium-pressure side, the high-pressure compressor can be used even more effectively if the low-pressure compressor is switched off. If the low-pressure compressor is in operation, it is advantageous if a check valve is disposed in the dehumidifier bypass, the check valve preventing the cooling agent from flowing back to the additional heat exchanger from the medium-pressure side. Depending on the saturated-steam pressure of the medium-pressure side, gaseous cooling agent could otherwise condense in the additional heat exchanger.

From the control device, an evaporation temperature at the additional heat exchanger can be lower than an evaporation temperature at the heat exchanger by means of controlling the expansion valve. In this case, therefore, it can be ensured that the air in the test space or the water contained therein is condensed at the additional heat exchanger and that water condensed at the heat exchanger does not freeze there. In this instance, the control device is intended to control a regulating valve of a regulating bypass of the cooling circuit as an additional measure.

It is particularly advantageous if pure carbon dioxide is used as the cooling agent. Pure carbon dioxide has a GWP of 1, is incombustible and cheaply available. Moreover, carbon dioxide is a pure substance and is azeotropic, which is the reason why the advantageous execution of the method and its variants are even possible. A cooling agent having a zeotropic behavior, in contrast, would hardly provide a sufficient amount of gaseous cooling agent at a very small difference in temperature and thus hardly allow regulating the capacity of the high-pressure compressor.

The test chamber according to the disclosure, in particular a climate chamber for conditioning air, comprises a temperature-insulated test space, which is sealable against an environment and serves for receiving test material, and a temperature control device for controlling the temperature of the test space, a temperature ranging from −20° C. to +180° C. being produced within the test space by means of the temperature control device, the temperature control device comprising a cooling device having a cooling circuit having carbon dioxide as a cooling agent, a heat exchanger the test space, a low-pressure compressor and a high-pressure compressor downstream of the low-pressure compressor, a gas cooler, a storage means for the cooling agent and an expansion valve, the test chamber comprising a control device for controlling and/or regulating the temperature in the test space. The cooling circuit comprises a high-pressure valve downstream of the gas cooler, the gaseous and/or liquid cooling agent being dosed in the storage means by means of the high-pressure valve, the storage means being connected to a medium-pressure side of the cooling circuit upstream of the high-pressure compressor and downstream of the low-pressure compressor via a medium-pressure bypass of the cooling circuit, the gaseous cooling agent being dosed in the medium-pressure side from the storage means by means of a medium-pressure valve when the low-pressure compressor is switched off. The description of advantages of the method according to the disclosure is referred to for the advantages of the test chamber according to the disclosure.

The temperature control device can comprise a heating device having a heater and a heating heat exchanger in the test space. The heating device can be an electric resistance heater, for example, which heats the heating heat exchanger in such a manner that an increase in temperature in the test space is enabled via the heating heat exchanger. If the heat exchanger and the heating heat exchanger can be controlled or regulated in a targeted manner for cooling or hating the air circulated in the test space by means of the control device, a temperature in the indicated temperature ranges can be produced within the test space by means of the temperature control device.

Further embodiments of a test chamber are derived from the description of features of the dependent claims referring back to method claim 1.

In the following, a preferred embodiment of the disclosure is described in more detail with reference to the attached drawings.

Figure 1:
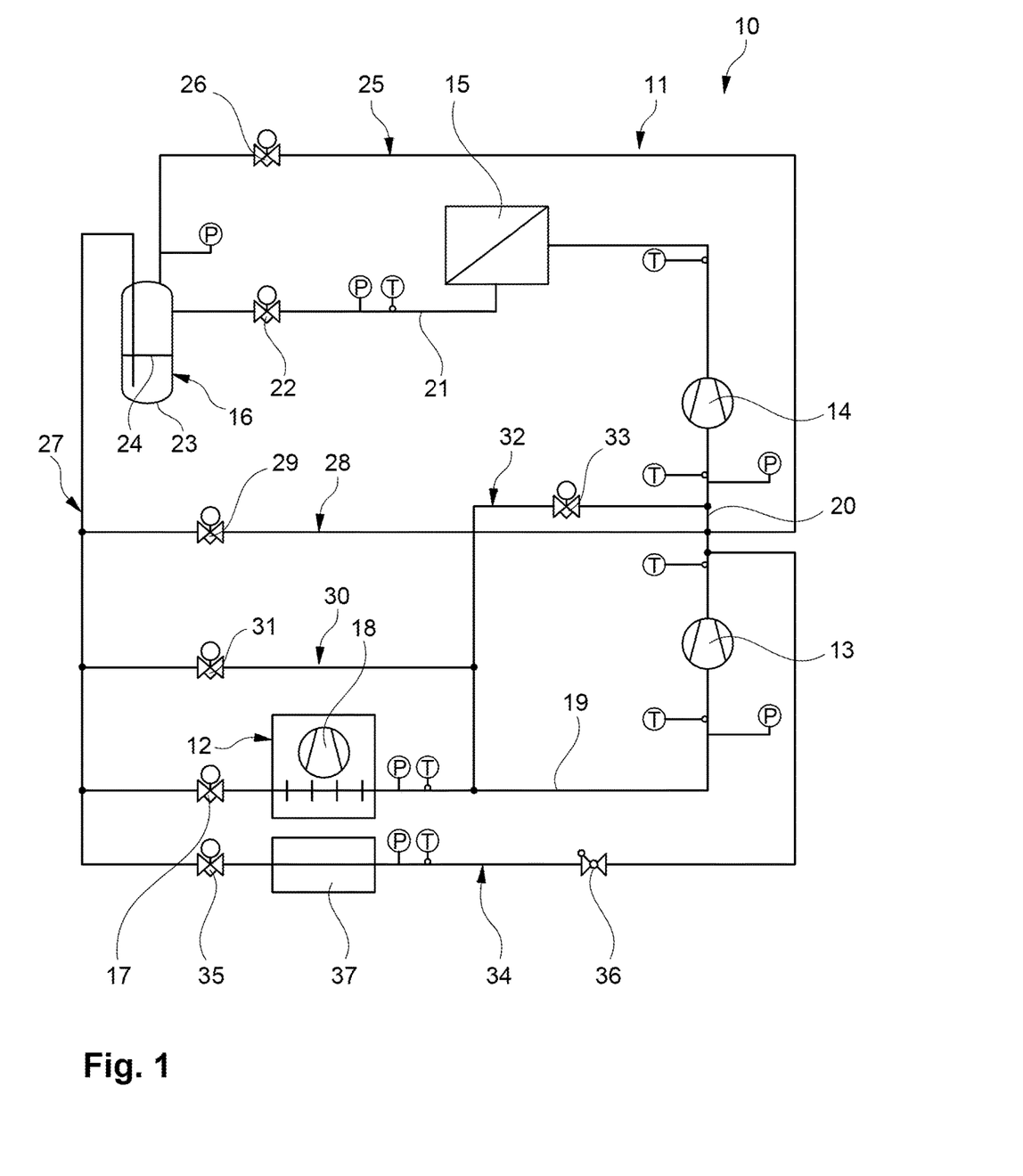
FIG. 1 shows a schematic illustration of an embodiment of a cooling circuit.

FIG. 1 shows a possible embodiment of a cooling device 10 of a test chamber (not illustrated). Cooling device 10 comprises a cooling circuit 11 having carbon dioxide ($CO_2$) as a cooling agent, a heat exchanger 12, a low-pressure compressor 13, a high-pressure compressor 14, a gas cooler 15, a storage means 16 and an expansion valve 17. Gas cooler 15 is realized like a heat exchanger and is cooled via a heat-exchanger medium, such as air or water. Heat exchanger 12 is disposed in an air-treatment channel (not illustrated) of the test chamber so that a fan 18 can circulate the air in the test space at heat exchanger 12. Furthermore, cooling circuit 11 comprises a low-pressure side 19, a medium-pressure side 10 and a high-pressure side 21. In low-pressure side 19, a pressure of the cooling agent is comparatively lower than in medium-pressure side 20. In medium-pressure side 20, a pressure of the cooling agent is comparatively lower than in high-pressure side 21.

Cooling circuit 11 further comprises a high-pressure valve 22 downstream of gas cooler 15 in the flow direction of the cooling agent, the gaseous and/or liquid cooling means being expanded or dosed in storage means 16 via high-pressure valve 22. Storage means 16 is realized as a pressure container 23 in which a phase boundary 24 is formed between the gaseous and the liquid cooling agent. A medium-pressure bypass 25 is connected to storage means 16 using a medium-pressure valve 26 of cooling circuit 11 so that the gaseous cooling means can be sampled from storage means 16 and be guided to medium-pressure side 20 downstream of low-pressure compressor 13 and high-pressure compressor 14 in the flow direction of the cooling agent. Furthermore, a line section 27 is connected in such a manner to storage means 16 that the liquid cooling agent can be sampled from storage means 16 and be guided to expansion valve 17.

Moreover, cooling circuit 11 comprises a second medium-pressure bypass 28 having a second medium-pressure valve 29, second medium-pressure bypass 28 being connected to line section 27 downstream of storage means 16 and to cooling circuit 11 downstream of low-pressure compressor 13 and upstream of high-pressure compressor 14. The liquid cooling agent can be dosed from storage means 16 in medium-pressure side 20 by means of second medium-pressure valve 29.

Furthermore, cooling circuit 11 comprises a low-pressure bypass 30 having a second expansion valve 31, low-pressure bypass 30 being connected to line section 27 downstream of storage means 16 and to low-pressure side 19 of cooling circuit 11 downstream of heat exchanger 12 and upstream of low-pressure compressor 13. The liquid cooling means can be dosed from storage means 16 in low-pressure side 19 by means of second expansion valve 31.

In cooling circuit 11, a regulating bypass 32 having a regulating valve is further realized, regulating bypass 32 being connected to low-pressure side 19 downstream of heat exchanger 12 and upstream of low-pressure compressor 13 in the flow direction of the cooling agent and to medium-pressure side 20 downstream of low-pressure compressor 13 and upstream of high-pressure compressor 14. The cooling agent can be guided from low-pressure side 19 to medium-pressure side 20 or vice versa from medium-pressure side 20 to low-pressure side 19 by means of regulating valve 33 as a function of an operating state of cooling circuit 11.

For dehumidifying the test space, cooling circuit 11 comprises a dehumidifier bypass 34 having a dehumidifier valve 35, a check valve 36 and an additional heat exchanger 37. Additional heat exchanger 37 is disposed in the test space (not illustrated). Dehumidifier bypass 34 is connected to storage device 16 via line section 27 and to medium-pressure side 20 downstream of low-pressure compressor 13 and high-pressure compressor 14. The liquid cooling agent can expand from storage means 16 in additional heat exchanger 37 and be guided to medium-pressure side 20 by means of dehumidifier valve 35. Additional heat exchanger 37 is cooled in such a manner that the water contained in the air in the test space essentially condenses at additional heat exchanger 37 and does not freeze at heat exchanger 12. Check valve 36 prevents a backflow of the cooling agent in additional heat exchanger 37 from medium-pressure side 20 if a pressure drops with respect to additional heat exchanger 37 because of an increase in pressure, e.g., via the operation of low-pressure compressor 13.

FIGS. 2 to 5 each show a pressure-enthalpy diagram (Log-p-h diagram) for the cooling agent circulating in cooling cycle 11 in different operating states of cooling circuit 11 when only high-pressure compressor 14 is in operation. In each diagram, the specific enthalpy is shown on the axis of abscissas and the logarithmically scaled pressure is shown on the axis of ordinate. A boiling curve 28 marks the transition from saturated liquid to wet steam, a vapor curve 39 marking a transition from wet steam to saturated steam. Boiling curve 38 and vapor curve 39 intersect at critical point 40.

Figure 2:
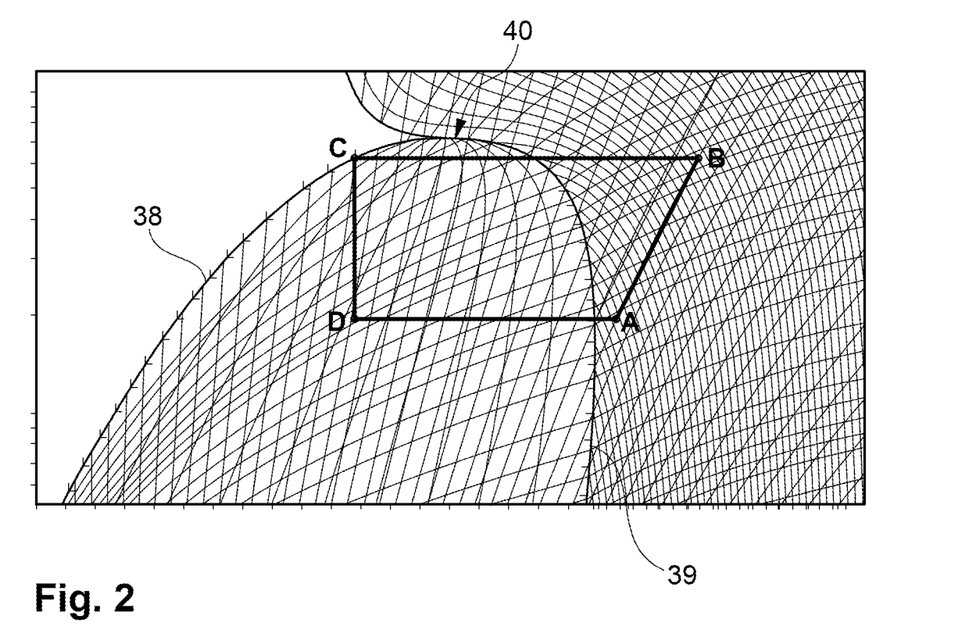
FIG. 2 shows a pressure-enthalpy diagram having a first operating state of a cooling cycle.

FIG. 2 shows a subcritical operating state of cooling circuit 11, the cooling agent being suctioned and compressed in this operating state using high-pressure compressor 14 starting from Point A of the cooling agent from low-pressure side 19 so that a pressure corresponding to Point B is attained downstream of compressor 14. The cooling agent is subsequently liquified in gas cooler 15 corresponding to Point C and guided to storage means 16 via high-pressure valve 22. In expansion valve 17, the cooling agent expands (Points C to D), the cooling agent evaporating in heat exchanger 12 (Points D to A).

Figure 3:
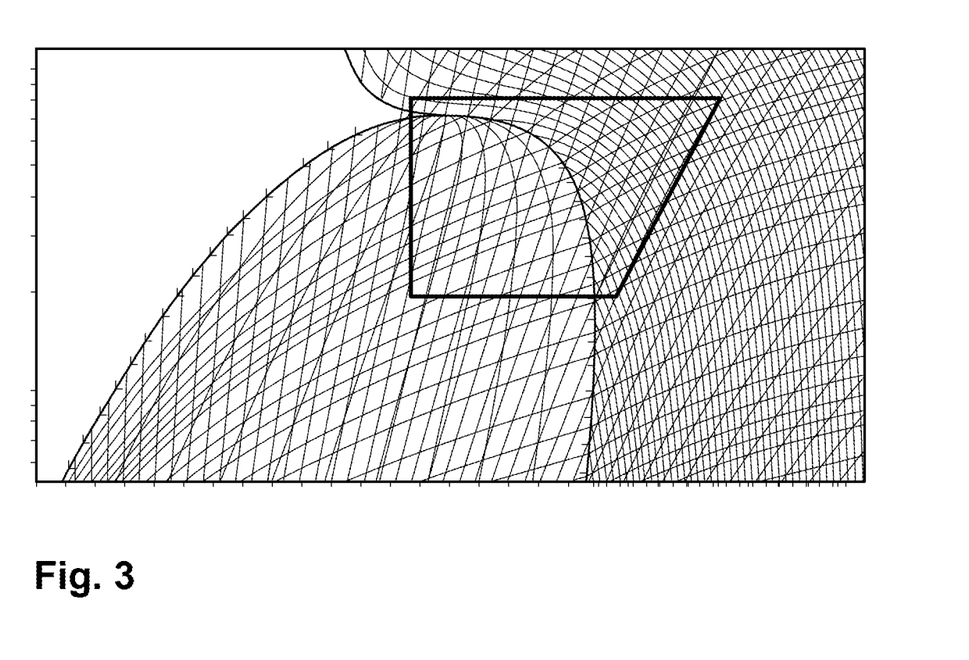
FIG. 3 shows the pressure-enthalpy diagram having a second operating state of the cooling cycle.
Figure 4:
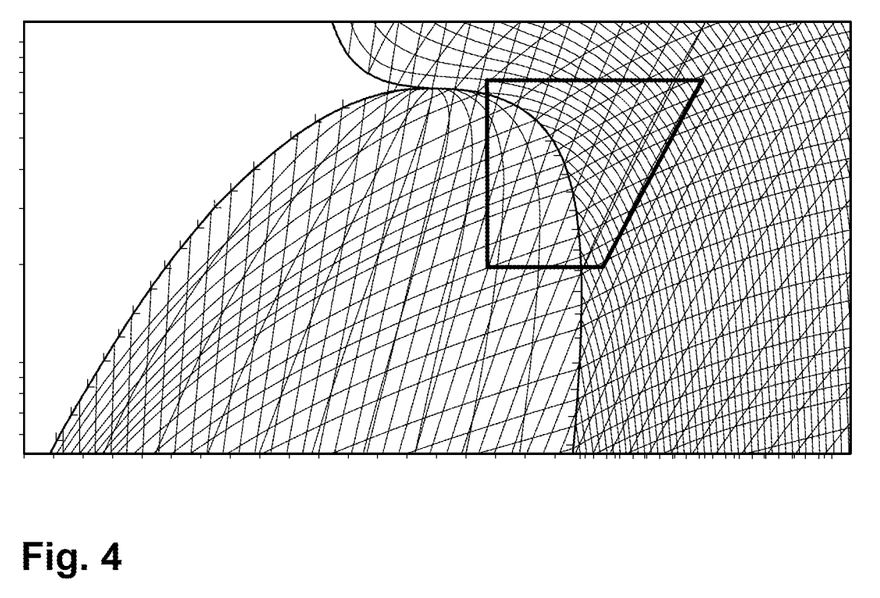
FIG. 4 shows the pressure-enthalpy diagram having a third operating state of the cooling cycle.
Figure 5:
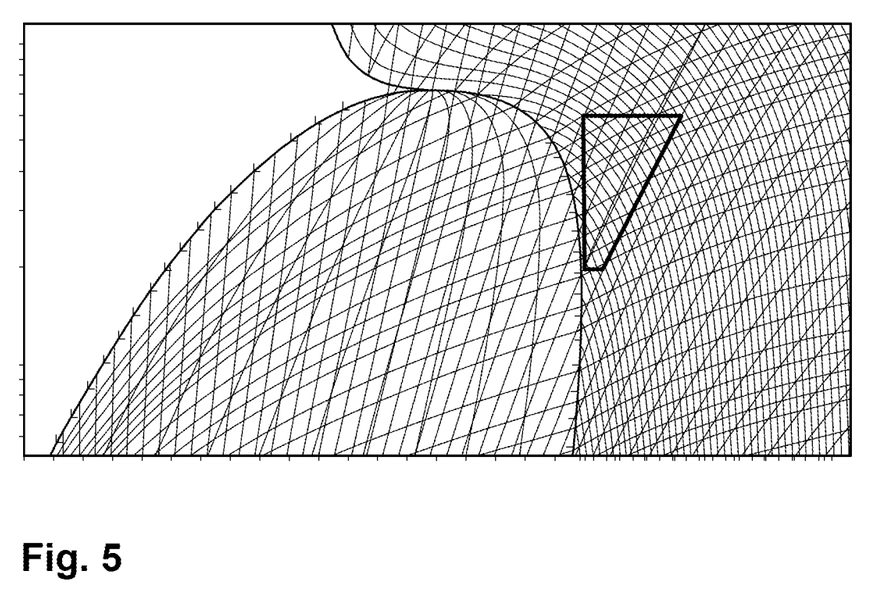
FIG. 5 shows the pressure-enthalpy diagram having a fourth operating state of the cooling cycle.

FIGS. 3 and 4 show transcritical operating states and FIG. 5 shows a supercritical operating state of cooling circuit 11 when only high-pressure compressor 14 is in operation.

The supercritical operating state is attained by low-pressure compressor 13 being switched off if no or very little cooling capacity is to be dissipated at heat exchanger 12 and/or a temperature of ≥10° C. is to be produced in the test space. The supercritical operating state is employed for producing the gaseous cooling means. For this purpose, a pressure is increased in the medium-pressure side 20 in which medium-pressure valve 26 is opened and the gaseous cooling agent is guided to medium-pressure side 20 via medium-pressure bypass 35. In addition, a conveyor capacity of high-pressure compressor 14 can first be lowered via a frequency converter. If no cooling capacity at all is required, expansion valve 17 and dehumidifier valve 35 are entirely closed, the cooling agent circulating only via medium-pressure bypass 25. In order to provide enough gaseous cooling agent in the supercritical operating state, high-pressure valve 22 is further opened so that more steam is produced via lowering the pressure in high-pressure side 21 when the cooling agent expands, the steam being able to be used for adjusting the capacity of high-pressure compressor 14. An exit temperature of the cooling agent at gas cooler 15 can also be increased and high-pressure valve 22 can be entirely opened so no liquid forms when the cooling agent expands and only gaseous cooling agent is circulated. Overall, switching off high-pressure compressor 14 is thus not required, meaning it can continue in operation, even if no or very little cooling capacity needs to be attained.

The invention claimed is:

1. A method for conditioning air in a temperature-insulated test space of a test chamber, which is sealable against an environment and serves for receiving test material, a temperature ranging from −20° C. to +180° C. being produced within the test space by means of a cooling device of a temperature control device of the test chamber, using a cooling circuit with carbon dioxide ($CO_2$) as a cooling agent, using a heat exchanger in the test space, using a low-pressure compressor and using a high-pressure compressor downstream of the low-pressure compressor, using a gas cooler, using a storage container for the cooling agent and using an expansion valve, the temperature in the test space being controlled and/or regulated by means of a control device of the test chamber, wherein a gaseous and/or liquid cooling agent is dosed in the storage container by means of a high-pressure valve of the cooling circuit downstream of the gas cooler, the storage container being connected to a medium-pressure side of the cooling circuit upstream of the high-pressure compressor and downstream of the low-pressure compressor via a medium-pressure bypass of the cooling circuit, the gaseous cooling agent being dosed in the medium-pressure side from the storage container by means of a medium-pressure valve when the low-pressure compressor is switched off.

2. The method according to claim 1, wherein a temperature ranging from −40° C. to +180° C. is produced within the test space by means of the temperature control device.

3. The method according to claim 1, wherein the low-pressure compressor is switched off by the control device at a target temperature ranging from −10° C. to +180° C.

4. The method according to claim 1, wherein the cooling circuit is operated in a thermodynamically subcritical, transcritical or supercritical operating state.

5. The method according to claim 4, wherein the high-pressure compressor and the low-pressure compressor are operated in at least the subcritical operating state.

6. The method according to claim 4, wherein in the supercritical state, the cooling agent expands at the high-pressure valve and is guided to the storage container as a gaseous cooling agent.

7. The method according to claim 4, wherein in the transcritical operating state, the high-pressure valve is regulated in such a manner by means of the control device that the at least partially gaseous and liquid cooling agent is guided to the storage container.

8. The method according to claim 4, wherein a capacity of the high-pressure compressor is adjusted as a function of a target temperature, the medium-pressure valve being regulated in such a manner in the supercritical operating state by means of the control device that the gaseous cooling agent is guided to the medium-pressure sided.

9. The method according to claim 1, wherein a second medium-pressure bypass having at least one second medium-pressure valve is disposed in the cooling circuit, the second medium-pressure bypass being connected to the cooling circuit downstream of the storage container and upstream of the expansion valve and downstream of the low-pressure compressor and upstream of the high-pressure compressor, the liquid cooling agent being dosed in the medium-pressure side from the storage means by means of the second medium-pressure valve.

10. The method according to claim 1, wherein a low-pressure bypass having at least one second expansion valve is disposed in the cooling circuit, the low-pressure bypass being connected to the cooling circuit downstream of the storage container and upstream of the expansion valve and downstream of the heat exchanger and upstream of the low-pressure compressor, the liquid cooling agent being dosed in a low-pressure side from the storage means by means of the second expansion valve.

11. The method according to claim 1, wherein a regulating bypass having at least one regulating valve is disposed in the cooling circuit, the regulating bypass being connected to the cooling circuit downstream of the heat exchanger and upstream of the low-pressure compressor and downstream of the low-pressure compressor and upstream of the high-pressure compressor, the gaseous cooling agent being dosed in a low-pressure side from the medium-pressure side by means of the regulating valve, the low-pressure compressor being in operation.

12. The method according to claim 11, wherein the control device sets a suction pressure upstream of the low-pressure compressor by means of the regulating bypass in such a manner that the cooling agent is in a state below the triple-point upstream of the low-pressure compressor.

13. The method according to claim 1, wherein a regulating bypass having at least one regulating valve is formed in the cooling circuit, the regulating bypass being connected to the cooling circuit downstream of the heat exchanger and upstream of the low-pressure compressor and downstream of the low-pressure compressor and upstream of the high-pressure compressor, the gaseous cooling agent being dosed in the medium-pressure side from a low-pressure side by means of the regulating valve, the low-pressure compressor being switched off.

14. The method according to claim 1, wherein the temperature control device comprises a dehumidifier which is made up of a dehumidifier bypass having a dehumidifier valve and an additional heat exchanger in the test space, the dehumidifier bypass being connected to the storage container and to the medium-pressure side downstream of the low-pressure compressor and upstream of the high-pressure compressor, the cooling agent being dosed in the medium-pressure side from the storage means by means of the dehumidifier valve when the low-pressure compressor is switched off or on.

15. The method according to claim 14, wherein the control device produces an evaporation temperature at the additional heat exchanger which is lower than an evaporation temperature at the heat exchanger by means of controlling the expansion valve and/or the dehumidifier valve.

16. The method according to claim 1, wherein pure carbon dioxide ($CO_2$) is used as the cooling agent.

17. A test chamber comprising a temperature-insulated test space, which is sealable against an environment and serves for receiving test material, and a temperature control device for controlling the temperature of the test space, a temperature ranging from −20° C. to +180° C. being produced within the test space by means of the temperature control device, the temperature control device comprising a cooling device having a cooling circuit with carbon dioxide ($CO_2$) as a cooling agent, a heat exchanger in the test space, a low-pressure compressor and a high-pressure compressor downstream of the low-pressure compressor, a gas cooler, a storage container for the cooling agent and an expansion valve, the test chamber comprising a control device for controlling and/or regulating the temperature in the test space, wherein the cooling circuit comprises a high-pressure valve downstream of the gas cooler, the gaseous and/or liquid cooling agent being dosed in the storage means by means of the high-pressure valve, the storage means being connected to a medium-pressure side of the cooling circuit upstream of the high-pressure compressor and downstream of the low-pressure compressor via a medium-pressure bypass of the cooling circuit, the gaseous cooling agent being dosed in the medium-pressure side from the storage means by means of a medium-pressure valve when the low-pressure compressor is switched off.

18. The test chamber according to claim 17, wherein the temperature control device comprises a heating device having a heater and a heating heat exchanger in the test space.

19. The method according to claim 1, wherein a temperature ranging from −55° C. to +180° C. is produced within the test space by means of the temperature control device.

20. The method according to claim 1, wherein the low-pressure compressor is switched off by the control device at a target temperature ranging from 0° C. to +180° C.

* * * * *

UNITED STATES PATENT AND TRADEMARK OFFICE
CERTIFICATE OF CORRECTION

PATENT NO. : 11,561,211 B2
APPLICATION NO. : 17/162697
DATED : January 24, 2023
INVENTOR(S) : Dennis Reuschel et al.

It is certified that error appears in the above-identified patent and that said Letters Patent is hereby corrected as shown below:

In the Claims

Column 11, Line 46, Claim 8, "sided." should be --side.--.

Signed and Sealed this
Fourth Day of April, 2023

Katherine Kelly Vidal
*Director of the United States Patent and Trademark Office*